United States Patent
Wu et al.

(10) Patent No.: US 10,684,337 B2
(45) Date of Patent: Jun. 16, 2020

(54) MULTIBAND RF/MRI PULSE DESIGN FOR MULTICHANNEL TRANSMITTER

(71) Applicants: Xiaoping Wu, Shoreview, MN (US); Pierre-Francois Van De Moortele, Minneapolis, MN (US); Sebastian Schmitter, Minneapolis, MN (US); Kamil Ugurbil, Minneapolis, MN (US); Edward Auerbach, Minneapolis, MN (US)

(72) Inventors: Xiaoping Wu, Shoreview, MN (US); Pierre-Francois Van De Moortele, Minneapolis, MN (US); Sebastian Schmitter, Minneapolis, MN (US); Kamil Ugurbil, Minneapolis, MN (US); Edward Auerbach, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 1210 days.

(21) Appl. No.: 14/762,093

(22) PCT Filed: Jan. 24, 2014

(86) PCT No.: PCT/US2014/013004
§ 371 (c)(1),
(2) Date: Jul. 20, 2015

(87) PCT Pub. No.: WO2014/116986
PCT Pub. Date: Jul. 31, 2014

(65) Prior Publication Data
US 2015/0362574 A1 Dec. 17, 2015

Related U.S. Application Data

(60) Provisional application No. 61/756,775, filed on Jan. 25, 2013, provisional application No. 61/914,775, filed on Dec. 11, 2013.

(51) Int. Cl.
*G01R 33/54* (2006.01)
*A61B 5/00* (2006.01)
(Continued)

(52) U.S. Cl.
CPC .......... *G01R 33/543* (2013.01); *A61B 5/0042* (2013.01); *A61B 5/055* (2013.01);
(Continued)

(58) Field of Classification Search
CPC .... A61B 5/0042; A61B 5/055; G01R 33/246; G01R 33/36; G01R 33/3607; G01R 33/4818; G01R 33/4835; G01R 33/543
(Continued)

(56) References Cited

U.S. PATENT DOCUMENTS

| 7,420,371 B2 | 9/2008 | Zhang |
| 7,800,368 B2 | 9/2010 | Vaughan et al. |

(Continued)

FOREIGN PATENT DOCUMENTS

| WO | 2012/088060 | 6/2012 |
| WO | 2012/088065 | 6/2012 |

OTHER PUBLICATIONS

Wu, Xiaoping, et al. "Simultaneous multislice multiband parallel radiofrequency excitation with independent slice-specific transmit B1 homogenization." Magnetic resonance in medicine 70.3 (Jun. 2013): 630-638. (Year: 2013).*

(Continued)

*Primary Examiner* — Rishi R Patel
(74) *Attorney, Agent, or Firm* — Quarles & Brady LLP (57) ABSTRACT

A method for designing one or more multichannel, multiband radio frequency ("RF") pulses for use with a magnetic resonance imaging ("MRI") system is provided. The method includes determining a number of RF amplitude modulations and a number of RF phase modulations for each (Continued)

channel in a multichannel RF coil by minimizing an objective function that includes a complex-valued vector. The objective function also contains a system matrix that accounts for both a spatial sensitivity profile of each channel in the multichannel RF coil and a magnetic field map for each excitation band in the multiband RF pulse.

17 Claims, 4 Drawing Sheets

(51) Int. Cl.
    *A61B 5/055*     (2006.01)
    *G01R 33/36*     (2006.01)
    *G01R 33/48*     (2006.01)
    *G01R 33/483*     (2006.01)
    *G01R 33/24*     (2006.01)

(52) U.S. Cl.
    CPC ......... *G01R 33/36* (2013.01); *G01R 33/4818* (2013.01); *G01R 33/4835* (2013.01); *G01R 33/246* (2013.01); *G01R 33/3607* (2013.01)

(58) Field of Classification Search
    USPC .......... 324/300–322; 600/407–435; 382/128–131
    See application file for complete search history.

(56) References Cited

U.S. PATENT DOCUMENTS

| | | | | |
|---|---|---|---|---|
| 8,148,985 B2* | 4/2012 | Zelinski | ............... | G01R 33/288 324/309 |
| 8,154,289 B2* | 4/2012 | Zelinski | ............. | G01R 33/4836 324/307 |
| 8,941,381 B2* | 1/2015 | Feinberg | ............ | G01R 33/4835 324/307 |
| 10,180,475 B2* | 1/2019 | Idiyatullin | ......... | G01R 33/4816 |
| 2009/0256570 A1* | 10/2009 | Zelinski | ............. | G01R 33/4836 324/314 |
| 2010/0066362 A1* | 3/2010 | Ullmann | ............ | G01R 33/4836 324/309 |
| 2010/0134105 A1* | 6/2010 | Zelinski | ............... | G01R 33/288 324/309 |
| 2012/0056620 A1* | 3/2012 | Feinberg | ............ | G01R 33/4835 324/309 |
| 2012/0268130 A1 | 10/2012 | Fautz et al. | | |
| 2015/0362574 A1* | 12/2015 | Wu | .................... | G01R 33/4835 324/322 |
| 2017/0074957 A1* | 3/2017 | Idiyatullin | ......... | G01R 33/4835 |

OTHER PUBLICATIONS

The International Search Report and Written Opinion dated May 14, 2014 for International Application No. PCT/US2014/013004.

* cited by examiner

K=2, N_slab=4

FIG. 2A

K=2, N_slab=4

FIG. 2B

K=2, N_slab=4

FIG. 3A

K=2, N_slab=4

MULTIBAND RF/MRI PULSE DESIGN FOR MULTICHANNEL TRANSMITTER

CROSS-REFERENCE TO RELATED APPLICATIONS

This application represents the U.S. National Stage of International Application No. PCT/US2014/013004, filed Jan. 24, 2014 which claims the benefit of U.S. Provisional Patent Application Ser. No. 61/756,775, filed on Jan. 25, 2013, and entitled "SYSTEM AND METHOD FOR MULTIBAND RADIO FREQUENCY MAGNETIC RESONANCE IMAGING PULSE DESIGN FOR USE WITH A MULTICHANNEL TRANSMITTER," and of U.S. Provisional Patent Application Ser. No. 61/914,775, filed on Dec. 11, 2013, and entitled "SYSTEM AND METHOD FOR MULTIBAND RADIO FREQUENCY MAGNETIC RESONANCE IMAGING PULSE DESIGN FOR USE WITH A MULTICHANNEL TRANSMITTER."

STATEMENT REGARDING FEDERALLY SPONSORED RESEARCH

This invention was made with government support under RR008079, EB015894, and MH091657 awarded by the National Institutes of Health. The government has certain rights in the invention.

BACKGROUND OF THE INVENTION

The field of the invention is systems and methods for magnetic resonance imaging ("MRI"). More particularly, the invention relates to systems and methods for designing, optimizing, and shimming multiband radio frequency ("RF") pulses for use in MRI.

The recent availability of high and ultrahigh magnetic fields in MRI, such as fields of 3 Tesla (3T) and 7 Tesla (7T), has enabled anatomical and functional MRI ("fMRI") studies of the human brain with increasingly higher spatial resolution and, in the case of fMRI applications, fidelity to sites of elevated neuronal activity. Obtaining such high-resolution fMRI data over the entire human brain, however, encounters the undesirable consequence of long volume repetition times ("TRs") even when single-shot slice acquisition methods, such as echo-planar imaging ("EPI"), are employed. Simultaneous multiband ("MB") RF excitation of multiple slices with subsequent unaliasing of the simultaneously acquired slices through parallel imaging principles using a multi-slice, two-dimensional EPI strategy has been used to address these problems. This method allows for a direct reduction in the volume TR by a factor (termed the MB factor) that is equal to the number of simultaneously excited slices.

The MB approach has been employed with significant success in task-based and in resting-state fMRI, leading to improved detection of resting state networks and new analysis strategies that reveal the temporal dynamics of such networks. The approach has also been employed to significantly reduce the otherwise very long imaging acquisition time in diffusion imaging techniques, such as high angular diffusion weighted imaging ("HARDI") and diffusion spectrum imaging ("DSI"). As such, the use of MB RF pulses has made the use of these imaging techniques practical and indispensable for efforts like the Human Connectome Project. In these applications, the achievable MB factors tolerated by the unaliasing process can be significantly improved through partial shifting of simultaneously acquired slices along the phase encode dimension using gradient blips in EPI. It is noted that the MB approach can be used with spatial encoding strategies other than EPI, such as gradient-recalled echoes acquired one k-space line at a time (e.g., FLASH), fast spin echo, and so on. In addition, the MB approach is applicable to imaging applications other than fMRI, including generally any imaging application in which multiple slices are acquired substantially simultaneously.

Despite these gains, however, the optimal use of the slice accelerated multiband approach at high (3T and 4T) and ultrahigh (7T and higher) fields is precluded by transmit B1 ("B1+") inhomogeneities and power deposition constraints. Signal-to-noise ratio ("SNR") and image contrast becomes spatially non-uniform and, at some locations, suboptimal due to non-uniform B1+ that arises as a result of the destructive interferences generated in the presence of the traveling wave behavior of RF at these field strengths. These B1+ inhomogeneities have been well documented at 4T and particularly at 7T, but are also sufficiently strong at 3T to cause SNR differences between the central and the peripheral parts of the brain, especially in a spin-echo ("SE") based sequence. Similarly, maximal achievable slice acceleration factors can be limited by power deposition especially at ultrahigh fields and/or when SE sequences are employed. When the number of slices and the volume TR are kept the same, the multiband approach does not deposit any more power compared to the conventional single slice excitation, even though peak power may increase quadratically with the MB factor; however, accelerating by the MB factor leads to MB-fold increase in power deposition, which imposes a limit on achievable accelerations.

These limitations are also paramount in imaging of the human torso and extremities in clinical diagnosis. In particular, imaging using sequences such as turbo spin echo, also known as fast spin echo and related derivatives, which are the basis of a large number of clinical scans in brain, torso, and extremities imaging, would suffer from power deposition and B1+ inhomogeneities when implemented with the multiband approach.

It would therefore be desirable to provide a method for designing and providing multiband RF pulses for multichannel transmission applications, in which the designed multiband RF pulses have reduced B1+ inhomogeneities and lowered power deposition (including lowered global SAR, lowered peak local SAR, and/or lowered peak RF power) as compared to currently available multichannel, multiband RF techniques.

SUMMARY OF THE INVENTION

The present invention overcomes the aforementioned drawbacks by providing a method for directing a magnetic resonance imaging ("MRI") system to generate a plurality of multiband radiofrequency ("RF") pulses. The method includes a precalculation stage, during which a multiband factor that defines a number of slices to be excited by each multiband RF pulse is selected, a number of multiband RF pulses to be designed is determined, and a plurality of slabs to be excited based on the selected multiband factor and the determined number of multiband RF pulses is determined. The method includes designing the multiband RF pulses by determining a number of RF amplitude modulations and a number of RF phase modulations for each channel in a multichannel RF coil. These values are determined by minimizing an objective function that includes a complex-valued vector that contains the RF pulse amplitude modulation and RF phase modulation for each pulse. The objective function also contains a system matrix that accounts for a spatial sensitivity profile of each channel in the multichannel RF coil, a magnetic field map for each excitation band in the multiband RF pulses, and a number of magnetic field gradients for each multiband RF pulse. The MRI system is directed to generate the multiband RF pulses using the RF amplitude modulation and RF phase modulation determined through such a minimization.

It is another aspect of the invention to provide a method for directing a magnetic resonance imaging ("MRI") system to generate a multiband radio frequency ("RF") pulse. The method includes designing the multiband RF pulse by determining an RF amplitude modulation and an RF phase modulation for each channel in a multichannel RF coil. These values are determined by minimizing an objective function that includes a complex-valued vector that contains the RF pulse amplitude modulation and RF phase modulation. The objective function also contains a system matrix that accounts for both a spatial sensitivity profile of each channel in the multichannel RF coil and a magnetic field map for each excitation band in the multiband RF pulse. The MRI system is directed to generate the multiband RF pulse using the RF amplitude modulation and RF phase modulation determined through such a minimization.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

A method for multichannel transmit ("pTx") multiband ("MB") pulse design that addresses the aforementioned problems of transmit B1 ("B1+") inhomogeneity and RF power deposition is provided. The method is capable of producing pTx MB pulse designs capable of providing significantly improved B1+ homogenization in multiple discrete slices simultaneously without necessitating the use of higher RF power relative to a single channel circularly polarized ("CP") mode application. The pulse designs are also capable of achieving savings in power deposition. Thus, the present invention is capable of improving B1 homogeneity for improved SNR and contrast-to-noise ratio ("CNR") while simultaneously reducing target power deposition, which may include global SAR, peak local SAR, and/or peak RF power.

In general, two strategies can be employed in multichannel MB excitation to find radio frequency ("RF") magnitude and phase modulations (i.e., RF shim values) of the base RF pulses so as to mitigate B1+ inhomogeneity. One strategy, herein referred to as a band-joint design, is to obtain a common set of channel-specific RF shim values for all M single-band ("SB") pulses that are combined to simultaneously excite M slices. This solution can be applied using a single channel transmitter that carries the MB pulse shapes, which is then split into multiple different channels and is subjected to a channel specific phase and amplitude change. In this approach, each of the M SB pulses of the MB pulse undergoes the same channel-specific phase and amplitude change. The other strategy, herein referred to as a band-specific design, is to calculate for each channel of the multi-channel transmitter a different set of shim values for each of the M SB pulses. Each of these approaches will be discussed now, in turn.

In the band-joint approach targeting uniform excitation (i.e. uniform |B1+|), the RF shim values for M-band Q-channel excitation can be obtained by solving the following magnitude least square problem:

$$\min_{w}\{|||Aw| - d||_2^2 + \lambda||w||_2^2\}; \quad (1)$$

where $$A = \begin{bmatrix} A_1 \\ A_2 \\ \vdots \\ A_M \end{bmatrix}; \quad (2)$$

and $$w = \begin{bmatrix} w_1 \\ w_2 \\ \vdots \\ w_Q \end{bmatrix}. \quad (3)$$

In Eqns. (1)-(3), A is a combined complex-valued matrix with $A_m$ (m=1, 2, ..., M) being the system matrix involving B1+ spatial sensitivity profiles of individual channels and the $\Delta B_0$ map for the $m^{th}$ band; W is a complex-valued vector with $w_q$ (q=1, 2, ..., Q) being the RF shim value for the $q^{th}$ channel; d is a scalar representing the desired transverse magnetization; and λ is a regularization parameter.

In the band-specific approach, one can solve:

$$\min_{w_{full}}\{|||A_{full}w_{full}| - d||_2^2 + \lambda||w_{full}||_2^2\}; \quad (4)$$

where $$A_{full} = \begin{bmatrix} A_1 & \cdots & 0 \\ \vdots & \ddots & \vdots \\ 0 & \cdots & A_M \end{bmatrix}; \quad (5)$$

and

-continued $$w_{full} = \begin{bmatrix} w_1 \\ w_2 \\ \vdots \\ w_M \end{bmatrix}. \quad (6)$$

In Eqns. (4)-(6), $A_{full}$ is a block diagonal matrix with $A_m$ being the diagonal element matrices and $w_{full}$ is a concatenated vector with $w_m$ (m=1, 2, ..., M) being a vector of RF shim values of individual channels for the $m^{th}$ band.

It is worth noting that the M base RF pulses that constitute the final summed MB pulse have different phase evolution through time (i.e., linear phase ramps of different slopes) introduced so as to target the frequency shift of each of the simultaneously excited M slices. Consequently, by Parseval's theorem, power deposition in a given time period is determined by the number of slices acquired, irrespective of whether the slices are acquired using an MB approach or a conventional single-slice excitation procedure. As a result, the use of the $\|w_{full}\|_2^2$ term is an optimum constraint for total RF power in band-specific pTx MB pulse design. Similarly, the following term could be used as an optimal constraint for global SAR:

$$\|S_0 w_{full}\|_2^2 \quad (7)$$

where $S_0$ is a global SAR matrix. It is also possible that peak local SAR management can be achieved in band-specific pTx MB pulse design by using a constraint that incorporates the final summed pulse shape into the constraint while simultaneously optimizing for more than one parameter, such as global SAR and peak local SAR.

It is also worth noting that in the band-specific pTx MB pulse design, the application of final RF pulses requires the independent control RF pulses of individual channels. This is because the final RF pulse per channel is the sum of M different base pulses each multiplied by a different weight and thus cannot be represented simply by a channel-specific weight, $w_q'$, multiplied by a common pulse.

By way of example, MB RF pulses can be designed as a single spoke (i.e., without gradient encoding in the transverse plane), or as more complex constructions (e.g., multiple spokes), to simultaneously excite the desired resonance frequency bands in a volume-of-interest with |B1+| homogenization. The unity target for such a pulse design may be defined as a homogeneous |B1+| in the desired slices. This target can be produced by manually creating a spatial mask that covers only the portions of the volume-of-interest in the bands. RF magnitude and phase modulations may be calculated using a variable exchange algorithm with the voxels outside the volume-of-interest not being considered in the pulse calculation. The target can also be something other than unity (i.e., uniform excitation) and can be tailored to achieve a specific, predefined spatial distribution of B1+ over the region-of-interest. For example, the target can be focused or "zoomed" to achieve high B1+ in a subregion or multiple subregions and low B1+ in other subregions.

RF pulses designed with a single spoke can also be employed for refocusing by scaling up the RF magnitudes to reach a 180 degree flip angle while still maintaining the same level of flip angle homogenization. However, when multiple spokes are desired for further improvement of the flip angle homogeneity, large tip angle pulse design methods, such as the optimal control approach, should be considered to sustain the excitation fidelity.

The MB RF pulses designed in this way can be constructed to cover a volume-of-interest, such as the human head or a subsection of the torso, with multiple slices at a time, with each group of slices having its own optimization dependent on the specific location of the slices manipulated in the volume-of-interest. The aforementioned design for the MB pulse can also incorporate static magnetic field, $B_0$, inhomogeneities for better pulse performance.

In a multiband imaging approach, multiple slices are excited simultaneously (or substantially simultaneously), subsequently acquired together, and finally unaliased to produce images corresponding to the individual slices. This process is repeated with a different set of slices to cover the volume-of-interest ("VOI"). If, for example, the desired resolution is 1 mm isotropic, the slice "thickness" is 1 mm. Thus, if the VOI has a dimension of 120 mm in the slice direction, 120 slices would be needed to cover the VOI using 1 mm isotropic resolution.

In conventional multislice approaches, each slice is excited and imaged separately in a two-dimensional acquisition, for example, using a readout gradient and a phase-encode gradient to encode the two orthogonal in-plane directions. Thus, in conventional multislice approaches 120 separate excitations and data acquisitions would be needed for the example stated above. With the multiband approach, using for example an MB factor of 4, the same VOI could be covered using only 30 excitations and subsequent data acquisitions. In this case, the pulse optimization described herein would be performed for the 30 sets of four discrete slices, not considering the potential variations in B1 and B0 along the slice thickness because it is small.

An alternative "hybrid" approach would be to excite not 1 mm slices, but thicker slabs, such as 10 mm thick slabs. An MB factor greater than one in this instance would correspond to substantially simultaneously exciting multiple slabs. For example, with an MB factor of 4, three sets of four-slab excitations would be used to cover the 120 mm thick VOI from the example above. In this instance, to obtain 1 mm isotropic resolution a three-dimensional acquisition would be used. In such an acquisition, a phase encoding dimension is added along the slab direction. In the example stated above, ten such phase encodings would be needed to obtain nominal 1 mm resolution along the 10 mm thick slab.

In the hybrid approach, a three-dimensional Fourier transform is used to resolve the slab into the 1 mm "slices" along the slab direction, as well as along the other two orthogonal directions. The simultaneously, or substantially simultaneously, excited "slabs" are then unaliased from each other using parallel imaging principles. In this acquisition scheme, pulse optimization for the "slab" selective pulses can be carried out as described above. Optionally, the B1 or B0 variation along the slab dimension could be ignored, while it is on average optimized in the place of the slab, as in the case acquiring individual thin slices. Using the hybrid imaging approach, however, the optimization could also take into account inhomogeneity in B1, or both B1 and B0 together, not only in the in-plane direction, as in the case of thin-slices, but also along the thickness of the slab.

Using pTx pulse designs for MB excitation can achieve the following benefits. First, the impact of B1+ inhomogeneities can be minimized. Second, other constraints can be achieved, such as minimizing local or global power deposition, which may be measured as a reduction in specific absorption rate ("SAR"). In one example, these advantages can be provided by exploiting a so-called 3D spoke slice-selective RF pulses with in-plane-only gradient blips. This approach allows for in-plane B1 homogenization while allowing the generation of a sharp slice profile. Furthermore, the management of the global and local SAR as well as average and peak RF power can also be incorporated into the pulse design, so as to comply with both technical and the safety constraints.

When obtaining MB data for a large volume-of-interest ("VOI"), such as the entire brain, many slices need to be excited and acquired, even when acquiring slices along the shortest morphologic dimension of the object being imaged. For example, to cover the whole human brain, including cerebrum, cerebellum, and brainstem, a total number of 104 slices will be required to fill up the typical dimension of 130 mm with a 1.25-mm spatial resolution along the slice dimension. With this many slices, the time required to obtain the B1+ profiles of individual transmit channels for each individual imaging slice and to perform the subsequent large-scale optimization problem to design a number of pTx MB RF pulses using the aforementioned slice-wise process may be impractically long for clinical applications.

For example, a 16-channel pulse design with the typical pulse design specifications (e.g., about 5 mm in-plane resolution and a single spoke for pulse optimization) for 104 slices will result in a 166400×1664 transfer matrix in the pulse design problem. Solving such a large optimization problem is a challenge, especially when additional constraints are included for power deposition. The computation time needed to find a satisfactory solution in this instance may be prohibitively long with the currently available computational resources.

Furthermore, with the current state of the art implementation of an MB pulse sequence, maintaining a large number of different pTx SB and pTx MB pulses as a result of the slice-specific pulse design may be difficult due to the limited maximum allowed memory allocation. For example, applying slice-specific pTx MB pulses to acquire 104 slices with an MB factor of 4 (i.e., M=4) may require the sequence to create and prepare a total number of 130 pTx pulses (104 pTx SB pulses plus 26 pTx MB pulses) for RF excitation. If the pulse sequence at hand is a spin echo sequence, then an additional 130 pulses for refocusing would be necessary. This number of pTx pulses would be difficult to maintain on current state-of-the-art MRI systems, which may be limited by their allowed memory allocation to a maximum number of RF pulses, such as a maximum number of 128 RF pulses. Even if there is no limit on the maximum number of RF pulses, applying a large number of slice-specific pTx pulses may not be time efficient because the pulse sequence preparation time scales with the number of the pTx pulses to be applied. Note that the use of a higher resolution will result in a larger number of slices, which in turn may promote further difficulties. Therefore, performing pTx MB pulse design in a slice-by-slice fashion for whole brain coverage may be very costly in time and computational requirements and may not be feasible in practice within the clinical time constraints with current instrumentation.

To address these problems, the aforementioned pulse design method can be adapted to provide an effective, efficient, and practical strategy for pTx MB RF pulse design for covering a large VOI, such as whole brain coverage. The following discussion utilizes the whole brain example for illustration purposes but is applicable for any large VOI coverage as may be employed in imaging of the torso or the entire human body.

In this adaptation of the method described above, no slice-by-slice pTx pulse design is conducted for the slices to be acquired for the data. Instead, pTx SB pulses that make up the pTx MB pulse are designed for a few slabs prescribed to cover the whole VOI. The number of slabs is determined by the number of pTx MB pulses desired, with a lower limit given by the MB factor. Additionally, the pulse design of each slab can be determined by considering only the B1+ information from a small number of gapped slices within the slab.

Using this adaptation of the method described above will drastically reduce the scale of the pulse design problem. For example, considering four slabs with four slices each to design a 16-channel, single-spoke pTx MB4 pulse (i.e. MB factor M=4) will reduce the size of the transfer matrix to 25600×64, a 169 fold reduction as compared to the size of 166400×1664 when using the slice-by-slice design approach with the same in-plane resolution.

The significant reduction in the size of the design problem will significantly decrease the computation time needed to find a satisfactory pulse solution. In addition, the use of only 16 slices in B1+ mapping and the use of only five pTx pulses (4 pTx SB pulses plus 1 pTx MB pulse) in the sequence will largely reduce the scanning time.

The method described above described using pTx RF pulses in a simultaneous multi-slice multiband acquisition so as to address the issues of increased B1+ inhomogeneity and RF power deposition at very high fields. That pTx MB pulse design can provide significantly improved B1+ uniformity (i.e., homogeneity) in multiple slices simultaneously in the human brain without necessitating the use of higher RF power relative to a single channel circularly polarized ("CP") mode application and/or achieve savings in power deposition.

However, as mentioned above, this approach would require long acquisition and computation times for whole brain coverage. Although such computational limits will undoubtedly be alleviated in the future with ever increasing computational power and network speeds, and acquisition speeds for mapping transmit B1 fields can be increased, practical implementations at the present can be achieved by adapting the aforementioned method.

In the adaptation of the aforementioned pTx pulse design method, a single or multiple pTx MB pulses can be designed to create uniform excitation within each individual acquisition slice over the entire VOI. The pulse design is not based on the B1+ information obtained from each of the slices that are to be acquired in the final MB acquisition; rather, it is based on the B1+ information obtained only from a few sparsely distributed slices within the VOI that are independent of the acquisition slices. The implementation of this design method includes two general stages: a pre-calculation stage and a calculation stage, which are discussed separately below.

The main purpose of the pre-calculation stage is to prescribe a few contiguous imaging slabs that encompass the VOI corresponding to individual pTx MB pulses to be designed. The pre-calculation stage then defines the slice placement within each slab, from which B1+ maps will be acquired for the subsequent pulse design. To this end, a two-step procedure is provided.

The first step is to determine the number, K, of pTx MB pulses to be designed, which together with the MB factor, M, gives the number of slabs, $N_{slab}$, that need to be prescribed, $$N_{slab} K \times M \tag{8}$$

The number of slabs, $N_{slab}$, should be viewed as K groups, each with M-slabs corresponding to a different pTx MB pulse. During data acquisition, each pTx MB pulse will be applied as in the conventional MB RF excitation to consecutively excite all the imaging slices residing in its M slabs by exciting M slices at a time, and the K pTx MB pulses will be played out one after another to excite all $N_{slab}$ slabs covering the entire VOI.

Figure 1A:
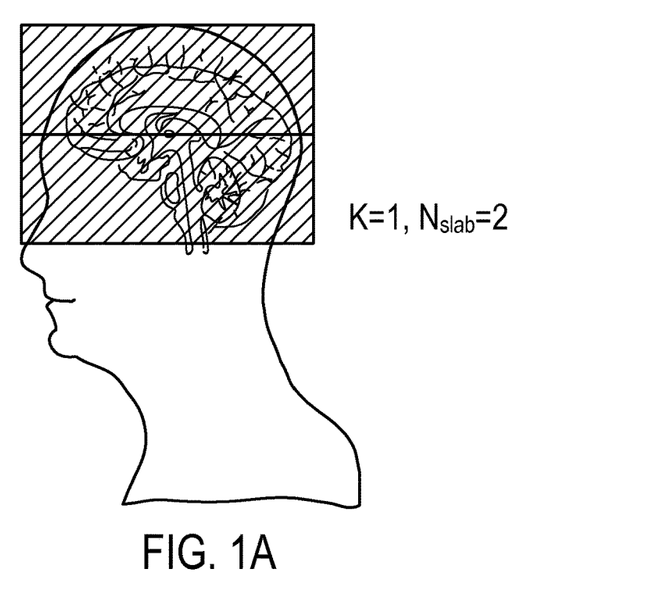
FIG. 1A is an example of a slab prescription for one multiband ("MB") radiofrequency ("RF") pulse, K=1, to excite two slabs, $N_{slab}$=2.
Figure 1B:
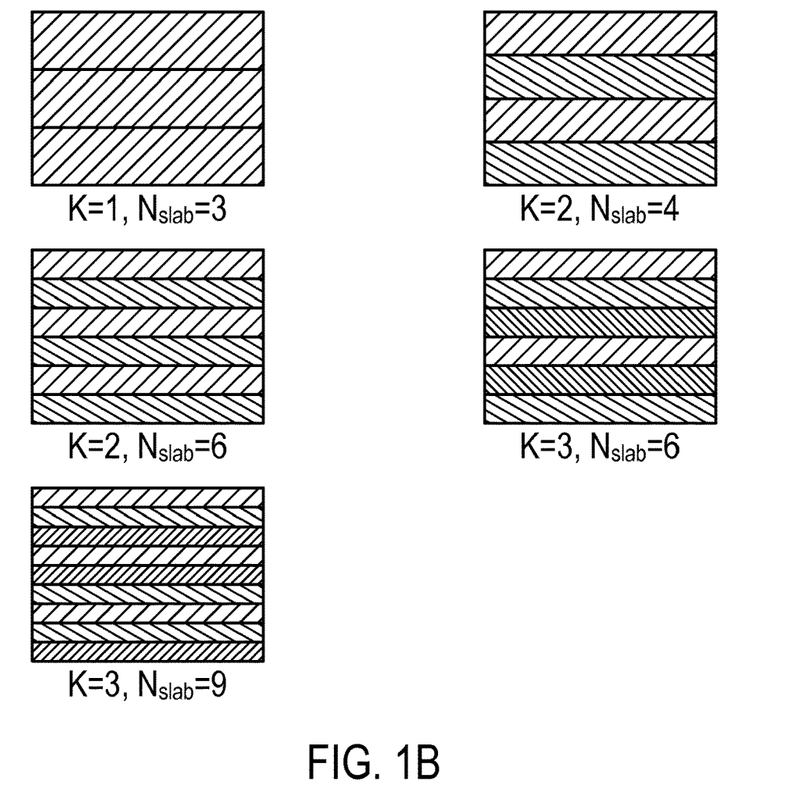
FIG. 1B shows examples of slab prescriptions for one MB RF pulse, K=1, to excite three slabs, $N_{slab}$=3; two MB RF pulses, K=2, to excite four slabs, $N_{slab}$=4; two MB RF pulses, K=2, to excite six slabs, $N_{slab}$=6; three MB RF pulses, K=3, to excite six slabs, $N_{slab}$=6; and three MB RF pulses, K=3, to excite nine slabs, $N_{slab}$=9.

FIGS. 1A and 1B illustrate example slab prescriptions for pTx MB2 and MB3 (i.e. MB factor M=2 and 3) RF pulse designs when acquiring simultaneous multislice multiband data from the whole brain with axial slices spanning the brain in the head-to-toe direction. As can be seen, for a given MB factor, different numbers of slabs may be considered, depending on how many pTx MB pulses are to be designed. A larger number of pTx MB pulses will result in a larger number of slabs. Note that the slab thickness only needs to be the same for the M slabs of the same MB pulse and does not have to be the same among different pTx MB pulses.

Figure 2A:
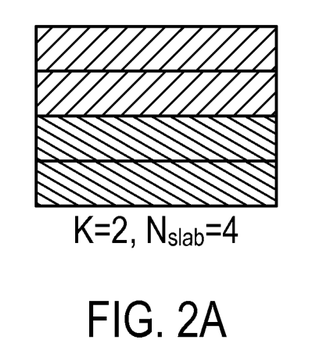
FIGS. 2A and 2B illustrate different slab prescriptions for two MB RF pulses, K=2, to excite four slabs, $N_{slab}$=4, in which the slab placements are not spatially interleaved.
Figure 2B:
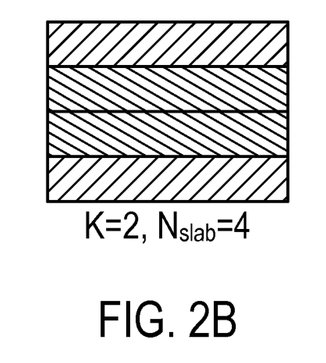

It should also be noted that all the slab prescriptions depicted in FIGS. 1A and 1B are placed in an interleaved manner with the maximum possible inter-slice distance that is constant across all the MB pulses, so as to achieve a globally optimum slice unaliasing in the subsequent MB reconstruction. However, the slab placement in general does not have to be interleaved and can be in any arbitrary order. For example, when prescribing four slabs for designing two pTx MB2 pulses, the two slabs of one pTx MB pulse can be sandwiched by, or can be stacked on top of, the two slabs of the other MB pulse, as illustrated in FIGS. 2A and 2B, respectively. Note that in the former case, the inter-slice distance is preferably different between the two MB pulses, regardless of the slab thickness used. On the other hand, in the latter case of stacking the slabs, the inter-slice distance can be the same for both MB pulses if the same slab thickness is assigned to all the four slabs.

Figure 3A:
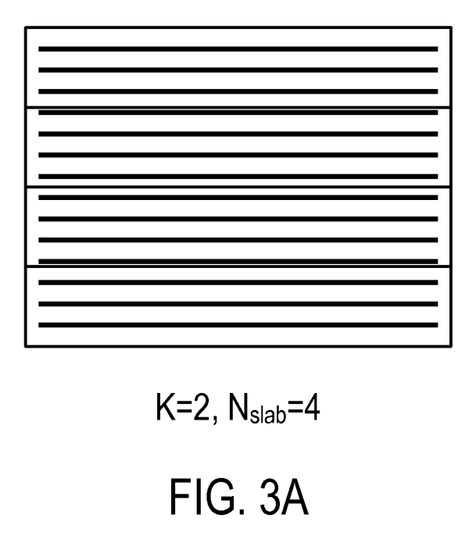
FIGS. 3A and 3B depict examples of slice placements within a slab.
Figure 3B:
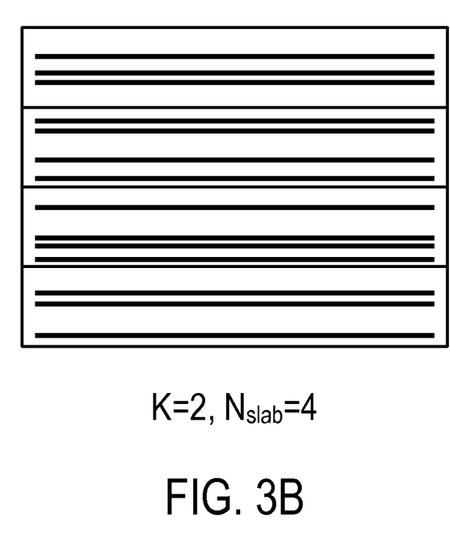

The second step in the pre-calculation stage is to design the B1+ slice placement within the individual slabs. This process includes determining the number of slices per slab and the distances in between the slices. FIGS. 3A and 3B depict two examples of slice placement within a slab. In the example illustrated in FIG. 3A, a total number of 14 slices are positioned inside the six slabs that have been prescribed for designing two pTx MB3 pulses, with a constant distance between slices and with the bordering slice shared by the two adjacent slabs. In the example illustrated in FIG. 3B, a different number of slices is placed in a randomized fashion within the six slabs. It should be noted that an optimum slice placement may be obtained by analyzing the B1+ variations along the slice selective direction based on electromagnetic simulations or experimentally acquired B1+ maps.

It is important to note that as the number of pTx MB pulses to be designed increases, the number of slabs to be prescribed will increase and the average slab thickness will decrease. When the number of pTx MB pulses reaches the total number of acquisition slices divided by the MB factor, the slab-wise pulse design will revert to the slice-wise design described above. For example, designing 26 pTx MB4 pulses in a slab-wise fashion for the acquisition of 104 slices is actually a slice-wise design because the 104 slabs that need to be prescribed will reduce to 104 slices coinciding with the 104 acquisition slices. This also means that the slice-wise pulse design described above can be viewed as a special case of the more generalized slab-wise design.

It is noted that the slabs can be derived from models of the object-of-interest, which may be the human brain. For example, the slabs can be derived from models such as a single human head model and/or a model derived as a composite or an average of many different subjects. The latter model can represent common average RF properties of the human head. By incorporating such model data, it is possible to obtain some pre-designed pTx RF pulses that account for inter-subject variability and may be used for different scans without further individual scans for B1+ mapping or pulse calculation.

Once the pre-calculation stage is finished, the calculation stage can be conducted to obtain the RF shim values that can reduce the B1+ inhomogeneity. Here, the aim is to design K number of pTx MB pulses that are different from one another. First, the generalized formulation of the pulse design problem with explicit constraints on RF power and SAR is provided. Then, two strategies for designing the individual pTx MB pulses are provided and the respective design problems in the small tip angle regime are outlined.

The generalized pulse design problem can be written as follows:

$$\min_w f_0(w) \quad (9);$$

subject to $$(1) f_1(w) \leq gSAR \quad (10);$$

$$(2) f_2(w) \leq lSAR \quad (11);$$

$$(3) f_3(w) \leq P_{ave} \quad (12);$$

$$(4) f_4(w) \leq P_{peak} \quad (13).$$

Here, the objective, $f_0$, typically represents the excitation error, and the unknown, w, is a complex valued vector concatenating the RF shim values for individual pTx MB spoke pulses. The four constraint functions, $f_{1-4}$, with respect to w denote the four most relevant RF power related quantities under concern and are used in inequality forms so as to impose explicit constraints upon (1) the global SAR, (2) the local SAR, (3) the total RF power, and (4) the instantaneous peak RF power, with gSAR, TSAR, $P_{ave}$ and $P_{peak}$ peak being the respective SAR and power limits. Solving such a constrained minimization problem results in trying to find a set of RF shim values that would provide the least achievable excitation error (i.e., the best achievable excitation fidelity) while ensuring that the resulting RF power and SAR numbers are within the respective prescribed limits.

For small tip angle pulse design, the objective function, $f_0$, is usually formulated as a square error, $\|Aw-d\|_2^2$, or a magnitude square error, $\|\,|Aw|-|d|\,\|_2^2$, to quantify the deviation of the resulting excitation pattern from the prescribed target pattern. Here A is a complex valued system matrix involving the multi-channel B1 field distributions normalized with respect to the input RF power of respective channels. The system matrix, A, also involves the main field inhomogeneities within all the slices prescribed, as well as the in-plane phase modulations (corresponding to the k-space placement of spokes) by gradient blips. The parameter, d, is a complex valued vector representing the desired excitation pattern (e.g., it can be a unity for a uniform excitation of a given flip angle). Furthermore, the system matrix A has a characteristic structure of being block diagonal and can be constructed as, $$A = \begin{bmatrix} A_1 & \cdots & 0 \\ \vdots & \ddots & \vdots \\ 0 & \cdots & A_K \end{bmatrix}; \quad (14)$$

where K is the number of pTx MB pulses to be designed, and the diagonal element matrix, $A_k$, is the system matrix for the $k^{th}$ pTx MB pulse design. Correspondingly, the vector, w, of unknowns and the vector, d, of the target are given by the following:

$$w = \begin{bmatrix} w_1 \\ w_2 \\ \vdots \\ w_K \end{bmatrix}; \quad (15)$$

and $$d = \begin{bmatrix} d_1 \\ d_2 \\ \vdots \\ d_K \end{bmatrix}; \quad (16)$$

respectively.

The use of such definitions of A, w and d in the objective function in the form of $\|Aw-d\|_2^2$ or $\|\,|Aw|-|d|\,\|_2^2$ coincides with the goal of the pulse design, which is to find a different set of RF shims for each of the K pTx MB pulses to be designed. However, the constructions of the individual system matrices, $A_k$ k=1, 2, ..., K, as well as the individual RF shim vectors $w_k$, are highly dependent on how the individual RF shim sets, $w_k$, will be calculated for each pTx MB pulse. As will be presented below, two possible design strategies exploiting different levels of degrees of freedom exist for the calculation of $w_k$, each with a different recipe for the formulation of the pulse design problem.

Two design strategies can be considered for the design of each individual pTx MB pulse. One strategy, defined here as the band-specific design, is to find a different RF shim set for each of the M pTx SB pulses that compose a pTx MB pulse. The other strategy, referred to as the band-joint design, is to find a common RF shim set for all of the M pTx SB pulses constituting a pTx MB pulse. Below, the design problem for the band-specific design is provided first, and the design problem for the band-joint design is provided after that.

Considering a constrained magnitude least square minimization, the pulse design problem derived from the generalized pulse design formulation for the band-specific design can be written as:

$$\min_{w_1, w_2, \ldots, w_K} \left\| \begin{bmatrix} A_1 & \cdots & 0 \\ \vdots & \ddots & \vdots \\ 0 & \cdots & A_K \end{bmatrix} \begin{bmatrix} w_1 \\ w_2 \\ \vdots \\ w_K \end{bmatrix} - \begin{bmatrix} d_1 \\ d_2 \\ \vdots \\ d_K \end{bmatrix} \right\|_2^2 ; \quad (17)$$

subject to, (1)

$$\left( \frac{\Delta t}{T} \sum_{i=1}^{N} |b(t_i)|^2 \right) \cdot \left( \sum_{k=1}^{K} N_k \cdot \sum_{m=1}^{M} \sum_{s=1}^{S} w_{(k,m,s)}^H Q w_{(k,m,s)} \right) \leq gSAR; \quad (18)$$

(2)

$$\left( \frac{\Delta t}{T} \sum_{i=1}^{N} |b(t_i)|^2 \right) \cdot \left( \sum_{k=1}^{K} N_k \cdot \sum_{m=1}^{M} \sum_{s=1}^{S} w_{(k,m,s)}^H S_v w_{(k,m,s)} \right) \leq lSAR, \quad (19)$$

$v = 1, 2, \ldots, V$ (3)

$$\left( \frac{\Delta t}{T} \sum_{i=1}^{N} |b(t_i)|^2 \right) \cdot \left( \sum_{k=1}^{K} N_k \cdot \sum_{m=1}^{M} \sum_{s=1}^{S} |w_{(k,m,c,s)}|^2 \right) \leq P_{ave}, \quad (20)$$

$c = 1, 2, \ldots, C;$ (4)

$$\|Mw_{(k,c,s)}\|_\infty^2 \leq P_{peak}, \quad (21)$$

$k = 1, 2, \ldots, K;$
$c = 1, 2, \ldots, C;$
$s = 1, 2, \ldots, S.$

Here the system matrix $A_k$ and the RF shim vector $w_k$ for the k-th pTx MB pulse are defined as, $$A_k = \begin{bmatrix} A_{k,1} & \cdots & 0 \\ \vdots & \ddots & \vdots \\ 0 & \cdots & A_{k,M} \end{bmatrix} \quad (22)$$

and $$w_k = \begin{bmatrix} w_{k,1} \\ w_{k,2} \\ \vdots \\ w_{k,M} \end{bmatrix},$$

$k = 1, 2, \ldots, K.$

Note that matrix $A_k$ is also constructed to be block-diagonal and this structure along with the corresponding definition of $w_k$ reflects the goal in the band-specific design of seeking a different RF shim set for each of the M pTx SB pulses corresponding to a given MB pulse. The individual diagonal element matrices of matrix $A_k$ and the individual element vectors of vector $w_k$ are further given by, $$A_{k,m} = [A_{k,m,1}, A_{k,m,2}, \ldots, A_{k,m,C}] \quad (23)$$

and;

$$w_{k,m} = \begin{bmatrix} w_{(k,m,1)} \\ w_{(k,m,2)} \\ \vdots \\ w_{(k,m,C)} \end{bmatrix}, \quad (24)$$

$m = 1, 2, \ldots, M,$
with;

$$A_{k,m,c} = [A_{k,m,c,1}, A_{k,m,c,2}, \ldots, A_{k,m,c,S}], ; \quad (25)$$

$$A_{k,m,c,s} = \begin{bmatrix} A_{k,m,c,s,1} \\ A_{k,m,c,s,2} \\ \vdots \\ A_{k,m,c,s,L(k,m)} \end{bmatrix}, \quad (26)$$

and;

$$w_{(k,m,c)} = \begin{bmatrix} w_{(k,m,c,1)} \\ w_{(k,m,c,2)} \\ \vdots \\ w_{(k,m,c,S)} \end{bmatrix}; \quad (27)$$

$c = 1, 2, \ldots, C;$ \quad (28)
$s = 1, 2, \ldots, S, ;$ where m, c and s count the bands, the transmit channels and the spokes, respectively; the matrix, $A_{k,m,c,s,l}$ (l=1, 2, ..., $L^{(k,m)}$), involves the spatially dependent phase accumulations at spoke s resulting from the in-plane gradient blips applied, as well as the B1+ field map of channel c within the l-th slice of all the $L^{(k,m)}$ slices that have been predefined for designing the m-th band of the k-th pTx MB pulse, and $w_{(k,m,c,s)}$ is a complex value representing the shim value for MB pulse k, band m, channel c and spoke s. Note that the total number of unknowns, which determines the degrees of freedom available in searching for an optimum solution, is thus (K×M×C×S) as given by the dimension of the overall shim vector w (i.e., the number of vector elements).

Correspondingly, the target vector $d_k$ is written as, $$d_k = \begin{bmatrix} d_{k,1} \\ d_{k,2} \\ \vdots \\ d_{k,M} \end{bmatrix} \quad (29)$$

with;

$$d_{k,m} = \begin{bmatrix} d_{k,m,1} \\ d_{k,m,2} \\ \vdots \\ d_{k,m,L^{(k,m)}} \end{bmatrix},$$

where $d_{k,m,l}$ is a vector representing the target excitation profile for slice l, band m, and pTx MB pulse k. It should be noted that matrix $A_{k,m}$, and vectors $w_{k,m}$ and $d_{k,m}$ as described above are those used in the conventional pTx spoke pulse design to calculate a single multi-channel multi-spoke RF shim set based either on a single slice (L=1) or simultaneously on multiple slices (L>1).

In the formulation of the four RF power and SAR related constraints, $w_{(k,m,s)}$ is the vertical concatenation of the shim values applied on all channels for MB pulse k, spoke s and band m (i.e., $w_{(k,m,s)} = [w_{(k,m,1,s)}, w_{(k,m,2,s)}, \ldots, w_{(k,m,C,s)}]^T$), whereas $w_{(k,c,s)}$ is the vertical concatenation of the shim values only applied on channel c for spoke s, but for all bands (i.e., $w_{(k,c,s)} = [w_{(k,m,1,s)}, w_{(k,m,2,s)}, \ldots, w_{(k,m,C,s)}]^T$)); Q is the global SAR matrix, and $\{S_v\}_{v=1,2,\ldots,V}$ denotes a set of V virtual observation points (VOPs) derived for estimation of local SAR (e.g., 10 gram SAR); it should be noted that these SAR matrices have incorporated all factors in the SAR calculation that are independent of the RF pulse including tissue properties and spatial averaging. Here, $N_k$ is the number of times that MB pulse k is applied in the MB data acquisition (e.g., in MB single-shot EPI, $\Sigma_{k=1}^{K} N_k M$ will give the total number of slices acquired), T is the time window for RF power averaging (e.g., it can be the repetition time used in the acquisition), $\Delta t$ is the dwell time of the RF pulse, and b(t) is the base pulse waveform (e.g., a conventional sinc pulse) defined with N time points. The matrix, M, is the matrix consisting of M conventional un-shimmed SB RF pulses, $a_m(t)$, m=1, 2, ..., M, and can be constructed as $$M = \begin{bmatrix} a_1(\Delta t) & a_2(\Delta t) & \ldots & a_M(\Delta t) \\ a_1(2\Delta t) & a_2(2\Delta t) & \ldots & a_M(2\Delta t) \\ \vdots & \vdots & \vdots & \vdots \\ a_1(N\Delta t) & a_2(N\Delta t) & \ldots & a_M(N\Delta t) \end{bmatrix}; \quad (30)$$

with $a_m(t) = b(t) \cdot \exp[-i\gamma G \cdot (m-1)z_0 \cdot t]$, where $\gamma$ is the gyromagnetic ratio, G is the maximum amplitude of the slice-selective gradient and $z_0$ is the inter-slice distance between the SB pulses.

It is important to note that the matrix-vector product, $Mw_{(k,c,s)}$, yields the final summed MB pulse shape of pTx MB pulse k at spoke s applied on channel c, with its maximum absolute value squared (i.e., $\|Mw_{(k,c,s)}\|^2_\infty$) giving the corresponding instantaneous peak RF power, and therefore, satisfying the $4^{th}$ inequality across all K pTx MB pulses, all C channels and all S spokes ensures that the instantaneous peak RF power of all the designed pTx MB pulses will be within the maximum peak power allowed by the RF power amplifier. Moreover, the pulse design formalism can be solved efficiently, e.g., via an interior point method.

It is also important to note that the application of the band-specific pTx MB pulses relies on a pTx system with fully independent multiple transmit channels (e.g., independent RF synthesizers, independent RF amplifiers) because the channel-specific RF waveforms are totally different from each other.

Similarly, the pulse design problem for the band-joint design can be formulated as:

$$\min_{w_1, w_2, \ldots, w_K} \left\| \begin{bmatrix} A_1 & \ldots & 0 \\ \vdots & \ddots & \vdots \\ 0 & \ldots & A_K \end{bmatrix} \begin{bmatrix} w_1 \\ w_2 \\ \vdots \\ w_K \end{bmatrix} - \begin{bmatrix} d_1 \\ d_2 \\ \vdots \\ d_K \end{bmatrix} \right\|^2_2; \quad (31)$$

subject to (1)

$$\left( \frac{\Delta t}{T} \sum_{i=1}^{N} |b(t_i)|^2 \right) \cdot \left( M \sum_{k=1}^{K} N_k \cdot \sum_{s=1}^{S} w_{(k,s)}^H Q w_{(k,s)} \right) \leq gSAR; \quad (32)$$

(2)

$$\left( \frac{\Delta t}{T} \sum_{i=1}^{N} |b(t_i)|^2 \right) \cdot \left( M \sum_{k=1}^{K} N_k \cdot \sum_{s=1}^{S} w_{(k,s)}^H S_v w_{(k,s)} \right) \leq lSAR, \quad (33)$$

$v = 1, 2, \ldots, V$ (3)

$$\left( \frac{\Delta t}{T} \sum_{i=1}^{N} |b(t_i)|^2 \right) \cdot \left( M \sum_{k=1}^{K} N_k \cdot \sum_{s=1}^{S} |w_{(k,c,s)}|^2 \right) \leq P_{ave}, \quad (34)$$

$c = 1, 2, \ldots, C;$ (4)

$$A_0^2 \cdot \|w_{(k,c,s)}\|^2_\infty \leq P_{peak}, \quad (35)$$
$k = 1, 2, \ldots, K;$
$c = 1, 2, \ldots, C;$
$s = 1, 2, \ldots, S.$ Since a common set of RF shims is calculated for all the M pTx SB pulses corresponding to a given MB pulse, each individual system matrix, $A_k$, is now constructed to be a stack of the lower level matrices, $A_{k,m}$, and is given by, $$A_k = \begin{bmatrix} A_{k,1} \\ A_{k,2} \\ \vdots \\ A_{k,M} \end{bmatrix}, \quad (36)$$

$k = 1, 2, \ldots, K,;$ with the individual matrices, $A_{k,m}$, defined with the same hierarchy structures as in the band-specific design. Correspondingly each individual vector $w_k$ now collapses in the m dimension and is given by $$w_k = \begin{bmatrix} w_{(k,1)} \\ w_{(k,2)} \\ \vdots \\ w_{(k,C)} \end{bmatrix}; \tag{37}$$

with $$w_{(k,c)} = \begin{bmatrix} w_{(k,c,1)} \\ w_{(k,c,2)} \\ \vdots \\ w_{(k,c,S)} \end{bmatrix},\tag{38}$$

$$k = 1, 2, \ldots, K;$$
$$c = 1, 2, \ldots, C.$$

Here $w_{(k,c,s)}$, s=1, 2, ..., S, is a complex number representing the shim value for all the M SB pulses of MB pulse k, applied on channel c and at spoke s. The target vectors $d_k$ have the same definitions as in the band-specific design. Note that in this case the degrees of freedom determined by the dimension of the overall shim vector, w, is only (K×C×S), an M fold reduction as compared to the band-specific design where the degrees of freedom is given by (K×M×C×S). Because of this degeneration of degrees of freedom, the joint design may not be as effective as the separate design in achieving the target excitation pattern while satisfying all the constraints.

Overall, the formulations of the four RF power and SAR constraints in the band-joint design are fairly similar to those in the band-specific design with most of the parameters being the same. Here two new parameters however are introduced. One is the vector, $w_{(k,s)}$, which is the vertical concatenation of the shim values applied on all channels for MB pulse k, spoke s but for all the M bands (i.e., $w_{(k,s)} = [w_{(k,1,s)}, w_{(k,2,s)}, \ldots, w_{(k,C,s)}]^T$), and the other is a scalar, $A_0$, which is the maximum amplitude of the sum of the M SB base pulses (i.e., $A_0 = \max_{i=1,2,\ldots,N} |\Sigma_{m=1}^{M} a_m(t_i)|$).

Despite of the similarity, two differences can be identified as compared to the band-specific design. The first difference resides in the first three constraints for the global SAR, the local SAR, and the total RF power. In the band-joint pulse design, the summation of the respective quantities over the SB pulses (indexed by m) reduces to a simple multiplication by the number M because all the M SB pulses now share a same shim value for a given MB pulse, a given channel, and a given spoke. This also results in the second difference, which can be seen in the last constraint imposed upon the instantaneous peak RF power. For the band-joint pulse design approach, in this constraint the peak power for a given MB pulse, a given channel, and a given spoke can now be simply provided by the product of two scalars, $A_0^2 \cdot |w_{(k,c,s)}|^2$, rather than a matrix vector multiplication incorporating the M base pulse shapes as in the band-specific design.

Unlike those band-specific pTx MB pulses, pTx MB pulses obtained from the band-joint design do not necessarily rely on full pTx capability and can possibly be applied just by using a simpler and less costly hardware that splits the single RF channel of the scanner into multiple channels at the low power stage and impose on the resulting separate channels a channel-specific phase and amplitude change.

For both the band-specific and band-joint pulse design approaches, the k-space placement of the spokes via in-plane gradient blips can further be optimized so as to achieve a better RF performance; however, such optimization is preferably performed on a per MB pulse basis, as opposed to a per slice basis when designing pTx pulses for sequential multi-slice excitation. In addition, although described above in the context of a constrained minimization with only four constraints, the aforementioned method for pTx MB RF pulse design may also be formulated as any other applicable optimization, such as a regularized minimization. The pulse design method may also include any other desired constraints, such as a constraint that constrains the change rate of the MB pulse envelope per channel.

The aforementioned method for MB RF pulse design may also be used to design time-shifted MB RF pulses, such as those described in co-pending patent application PCT/US2012/58541, which is herein incorporated by reference in its entirety; or to design MB RF pulses with lower power deposition, such as those described in co-pending patent application PCT/US2011/066081, which is herein incorporated by reference in its entirety; or to design large tip angle MB RF pulses using, as an example, an optimal control method; or to design RF pulses that can be employed to control aliasing conditions, such as those that may be used in a CAIPIRINHA ("Controlled Aliasing In Parallel Imaging Results IN Higher Acceleration") technique, with improved imaging performance.

In general, for an MB experiment with M-fold acceleration, M single-band RF waveforms can be used to generate the final MB RF waveform. In the simplest case, the same basic RF shape (e.g., a sinc waveform) is used for each frequency band, but a different frequency offset is applied to each band by modulating the phase of waveform. This frequency offset defines the band spacing. The complex sum of the M single-band waveforms is computed to generate one multi-band waveform. The single-band waveforms can be used to acquire reference scan data, and the multi-band waveform can be used for an accelerated data acquisition. In some embodiments, for a multi-slice and multi-band acquisition, these M+1 RF waveforms are applied sequentially with N different transmitter frequency offsets (the main transmit frequency dynamically modified by the scanner) to acquire a total of N×M slices. For the implementation of pTx MB pulses, there are several possible ways to extend this basic scheme to take advantage of multiple transmit channels, as described below.

In one example, a single pTx MB pulse is designed using a single spoke trajectory in excitation k-space. In this example, the same basic pulse shape (e.g., a sinc waveform) is used for each band, with a different frequency offset applied to each band the same way as described above. A transmit channel-specific global magnitude and phase is then applied on top of each of the M single-band RF waveforms. The complex sum of these waveforms is computed to generate a transmit channel-specific multi-band waveform. Now there are M+1 waveforms for each transmit channel, or T×(M+1) waveforms in total, with T being the number of transmit channels. Note that each group of M+1 waveforms can be computed in parallel, which saves time in practice. Again, for a multi-slice and multi-band acquisition, these waveforms are applied sequentially with N different transmitter frequency offsets to acquire a total of N×M slices.

In another example, multiple different pTx MB pulses can be designed using a single spoke trajectory in excitation k-space. In such instances, instead of calculating only T×(M+1) RF waveforms and reusing these N times with different transmitter frequencies, up to N×T sets of transmit channel-specific magnitudes and phases can be determined and used to calculate N×T×(M+1) waveforms to excite the N×M slices. In practice, because the N groups of single-band waveforms for each transmit channel only differ in terms of global magnitude and phase, only one set needs to be retained and the rest can be replicated by having the scanner modify the main transmit frequency, RF magnitude, and RF phase dynamically. So it would only be necessary to load M+N unique waveforms for each transmit channel, or T×(M+N) waveforms in total. This is important considering the limited memory that may be available for storing waveforms on the scanner.

The abovementioned schemes can readily be extended for pTx MB pulse design using multiple spokes trajectories in excitation k-space, in which case it is possible to subdivide the entire multi-spoke RF shapes into a few segments to form individual "spoke" pulses, with transmit-channel specific magnitudes and phases for each spoke. Additionally, it is also possible to not use a different pulse waveform shape for different excitation band or slice location.

Practical considerations that may influence the choice of pulse design strategy include the computational speed and system memory available to store pulse waveforms. Although it is possible to calculate a unique waveform for every channel, for each band, for each slice location, and for each k-space spoke, etc, the number of unique waveforms that may be pre-calculated and used in a sequence on a standard clinical scanner may be limited (e.g., 128 per transmit channel). In some instances, calculating and uploading waveforms may also be a relatively slow process. For a practical implementation, it may be preferable to to minimize the number of unique waveforms, which the schemes above are designed to do.

Figure 4:
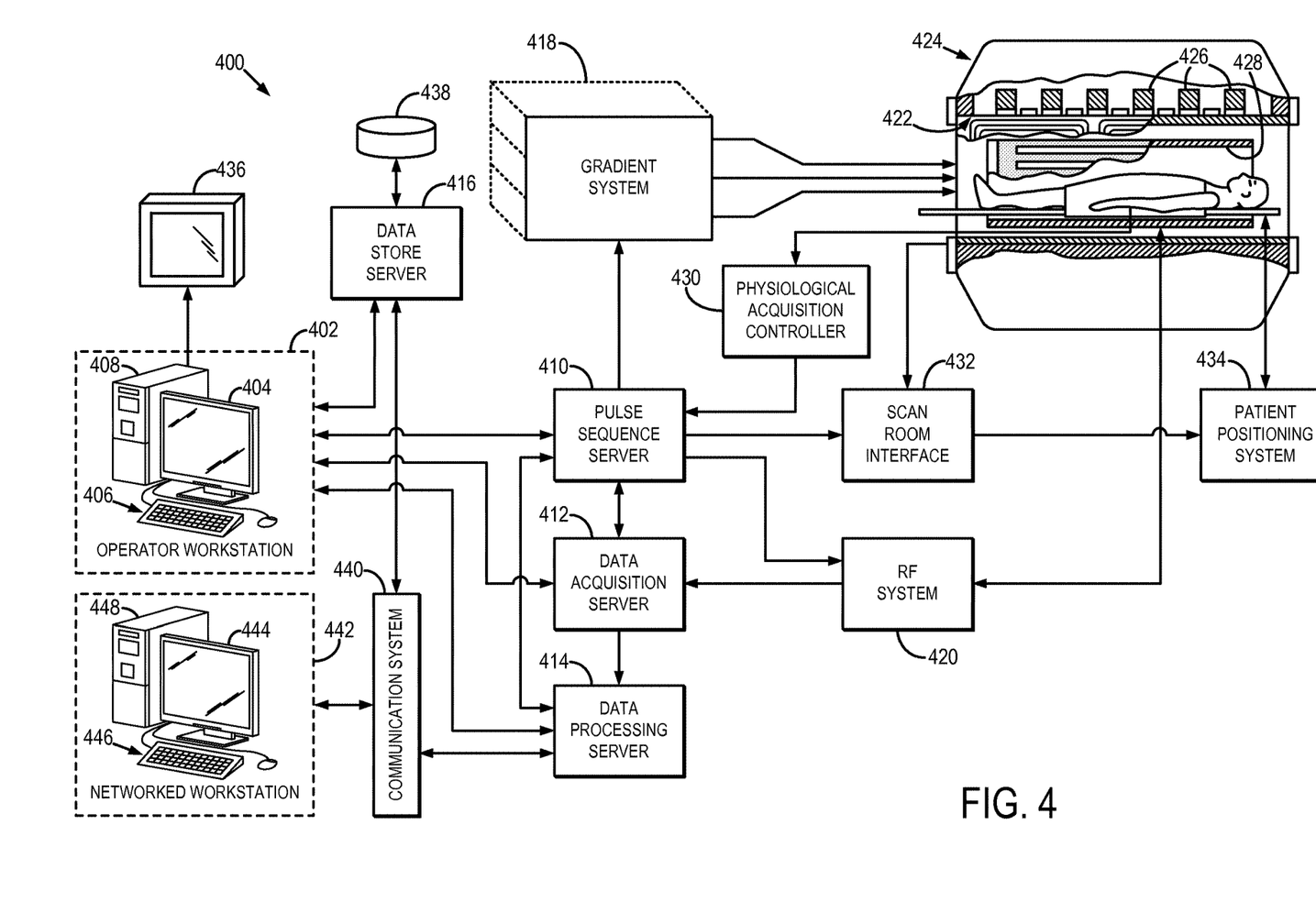
FIG. 4 is a block diagram of an example of a magnetic resonance imaging ("MRI") system.

Referring particularly now to FIG. 4, an example of a magnetic resonance imaging ("MRI") system 400 is illustrated. The MRI system 400 includes an operator workstation 402, which will typically include a display 404; one or more input devices 406, such as a keyboard and mouse; and a processor 408. The processor 408 may include a commercially available programmable machine running a commercially available operating system. The operator workstation 402 provides the operator interface that enables scan prescriptions to be entered into the MRI system 400. In general, the operator workstation 402 may be coupled to four servers: a pulse sequence server 410; a data acquisition server 412; a data processing server 414; and a data store server 416. The operator workstation 402 and each server 410, 412, 414, and 416 are connected to communicate with each other. For example, the servers 410, 412, 414, and 416 may be connected via a communication system 440, which may include any suitable network connection, whether wired, wireless, or a combination of both. As an example, the communication system 440 may include both proprietary or dedicated networks, as well as open networks, such as the internet.

The pulse sequence server 410 functions in response to instructions downloaded from the operator workstation 402 to operate a gradient system 418 and a radiofrequency ("RF") system 420. Gradient waveforms necessary to perform the prescribed scan are produced and applied to the gradient system 418, which excites gradient coils in an assembly 422 to produce the magnetic field gradients $G_x$, $G_y$, and $G_z$ used for position encoding magnetic resonance signals. The gradient coil assembly 422 forms part of a magnet assembly 424 that includes a polarizing magnet 426 and a whole-body RF coil 428. The whole-body RF coil 428 may include a single-channel transmit coil or a multiple-channel transmit coil array that is capable of implementing the method of the present invention. For instance, the whole-body RF coil 428 may include a two channel transmit coil array.

RF waveforms are applied by the RF system 420 to the RF coil 428, or a separate local coil (not shown in FIG. 4), in order to perform the prescribed magnetic resonance pulse sequence. Responsive magnetic resonance signals detected by the RF coil 428, or a separate local coil (not shown in FIG. 4), are received by the RF system 420, where they are amplified, demodulated, filtered, and digitized under direction of commands produced by the pulse sequence server 410. The RF system 420 includes one or more RF transmitters for producing a wide variety of RF pulses used in MRI pulse sequences. The RF transmitter is responsive to the scan prescription and direction from the pulse sequence server 410 to produce RF pulses of the desired frequency, phase, and pulse amplitude waveform. The generated RF pulses may be applied to the whole-body RF coil 428 or to one or more local coils or coil arrays (not shown in FIG. 4).

The RF system 420 also includes one or more RF receiver channels. Each RF receiver channel includes an RF preamplifier that amplifies the magnetic resonance signal received by the coil 428 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M = \sqrt{I^2 + Q^2} \tag{39}$$

and the phase of the received magnetic resonance signal may also be determined according to the following relationship:

$$\varphi = \tan^{-1}\left(\frac{Q}{I}\right). \tag{40}$$

The pulse sequence server 410 also optionally receives patient data from a physiological acquisition controller 430. By way of example, the physiological acquisition controller 430 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 410 to synchronize, or "gate," the performance of the scan with the subject's heart beat or respiration.

The pulse sequence server 410 also connects to a scan room interface circuit 432 that receives signals from various sensors associated with the condition of the patient and the magnet system. It is also through the scan room interface circuit 432 that a patient positioning system 434 receives commands to move the patient to desired positions during the scan.

The digitized magnetic resonance signal samples produced by the RF system 420 are received by the data acquisition server 412. The data acquisition server 412 operates in response to instructions downloaded from the operator workstation 402 to receive the real-time magnetic resonance data and provide buffer storage, such that no data is lost by data overrun. In some scans, the data acquisition server 412 does little more than pass the acquired magnetic resonance data to the data processor server 414. However, in scans that require information derived from acquired magnetic resonance data to control the further performance of the scan, the data acquisition server 412 is programmed to produce such information and convey it to the pulse sequence server 410. For example, during prescans, magnetic resonance data is acquired and used to calibrate the pulse sequence performed by the pulse sequence server 410. As another example, navigator signals may be acquired and used to adjust the operating parameters of the RF system 420 or the gradient system 418, or to control the view order in which k-space is sampled. In still another example, the data acquisition server 412 may also be employed to process magnetic resonance signals used to detect the arrival of a contrast agent in a magnetic resonance angiography ("MRA") scan. By way of example, the data acquisition server 412 acquires magnetic resonance data and processes it in real-time to produce information that is used to control the scan.

The data processing server 414 receives magnetic resonance data from the data acquisition server 412 and processes it in accordance with instructions downloaded from the operator workstation 402. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 414 are conveyed back to the operator workstation 402 where they are stored. Real-time images are stored in a data base memory cache (not shown in FIG. 4), from which they may be output to operator display 412 or a display 436 that is located near the magnet assembly 424 for use by attending physicians. Batch mode images or selected real time images are stored in a host database on disc storage 438. When such images have been reconstructed and transferred to storage, the data processing server 414 notifies the data store server 416 on the operator workstation 402. The operator workstation 402 may be used by an operator to archive the images, produce films, or send the images via a network to other facilities.

The MRI system 400 may also include one or more networked workstations 442. By way of example, a networked workstation 442 may include a display 444; one or more input devices 446, such as a keyboard and mouse; and a processor 448. The networked workstation 442 may be located within the same facility as the operator workstation 402, or in a different facility, such as a different healthcare institution or clinic.

The networked workstation 442, whether within the same facility or in a different facility as the operator workstation 402, may gain remote access to the data processing server 414 or data store server 416 via the communication system 440. Accordingly, multiple networked workstations 442 may have access to the data processing server 414 and the data store server 416. In this manner, magnetic resonance data, reconstructed images, or other data may be exchanged between the data processing server 414 or the data store server 416 and the networked workstations 442, such that the data or images may be remotely processed by a networked workstation 442. This data may be exchanged in any suitable format, such as in accordance with the transmission control protocol ("TCP"), the internet protocol ("IP"), or other known or suitable protocols.

Figure 5:
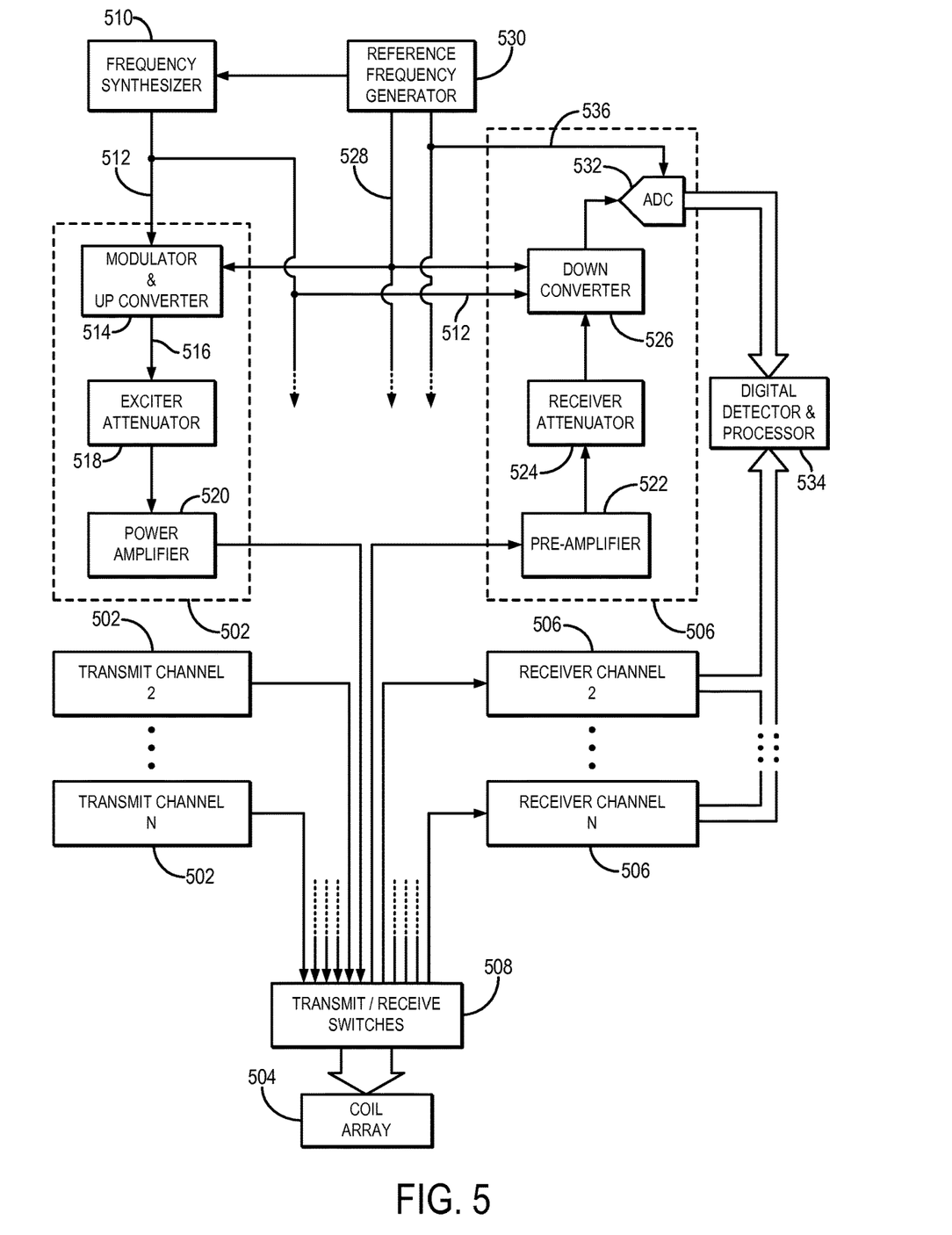
FIG. 5 is a block diagram of an example of a radio frequency ("RF") system that may form a part of the MRI system of FIG. 4 and that includes a multichannel transmitter and receiver.

As shown in FIG. 4, the RF system 420 may be connected to the whole-body RF coil 428, or, as shown in FIG. 5, a transmission section of the RF system 420 may connect to one or more transmit channels 502 of an RF coil array 504 and a receiver section of the RF system 420 may connect to one or more receiver channels 506 of the RF coil array 504. The transmit channels 502 and the receiver channels 506 are connected to the RF coil array 504 by way of one or more transmit/receive ("T/R") switches 508. In alternative configurations of the RF system 428 in which the receive coils are a separate collection of coils than the transmit coils, T/R switches 508 are not needed and are not used. Instead, in such a configuration the receive array is "detuned" during transmission so that it does not couple to the transmitter. Likewise, during reception, the transmitter is detuned. In this manner, the transmit and receive paths do not mix.

Referring particularly to FIG. 5, the RF system 420 includes one or more transmit channels 502 that produce a prescribed RF excitation field. The base, or carrier, frequency of this RF excitation field is produced under control of a frequency synthesizer 510 that receives a set of digital signals from the pulse sequence server 410. These digital signals indicate the frequency and phase of the RF carrier signal produced at an output 512. The RF carrier is applied to a modulator and up converter 514 where its amplitude is modulated in response to a signal, R(t), also received from the pulse sequence server 410. The signal, R(t), defines the envelope of the RF excitation pulse to be produced and is produced by sequentially reading out a series of stored digital values. These stored digital values may be changed to enable any desired RF pulse envelope to be produced.

The magnitude of the RF excitation pulse produced at output 516 may be attenuated by an exciter attenuator circuit 518 that receives a digital command from the pulse sequence server 410. The attenuated RF excitation pulses are then applied to a power amplifier 520 that drives the RF coil array 504.

The MR signal produced by the subject is picked up by the RF coil array 502 and applied to the inputs of the set of receiver channels 506. A preamplifier 522 in each receiver channel 506 amplifies the signal, which is then attenuated by a receiver attenuator 524 by an amount determined by a digital attenuation signal received from the pulse sequence server 410. The received signal is at or around the Larmor frequency, and this high frequency signal is down converted in a two step process by a down converter 526. The down converter 526 first mixes the MR signal with the carrier signal on line 512 and then mixes the resulting difference signal with a reference signal on line 528 that is produced by a reference frequency generator 530. The down converted MR signal is applied to the input of an analog-to-digital ("A/D") converter 532 that samples and digitizes the analog signal. As an alternative to down conversion of the high frequency signal, the received analog signal can also be detected directly with an appropriately fast analog-to-digital ("A/D") converter and/or with appropriate undersampling. The sampled and digitized signal is then applied to a digital detector and signal processor 534 that produces 16-bit in-phase (I) values and 16-bit quadrature (Q) values corresponding to the received signal. The resulting stream of digitized I and Q values of the received signal are output to the data acquisition server 412. In addition to generating the reference signal on line 528, the reference frequency generator 530 also generates a sampling signal on line 536 that is applied to the A/D converter 532.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for directing a magnetic resonance imaging (MRI) system to generate a multiband radio frequency (RF) pulse, the steps of the method comprising:
   a) determining an RF amplitude modulation and an RF phase modulation for each channel in a multichannel RF coil by minimizing an objective function that includes:
      a complex-valued vector containing the RF amplitude modulation and RF phase modulation; and
      a system matrix that accounts for both a spatial sensitivity profile of each channel in the multichannel RF coil and a magnetic field map for each excitation band in the multiband RF pulse; and
   b) directing the MRI system to generate at least one multiband RF pulse using the RF amplitude modulations and RF phase modulations determined in step a).

2. The method as recited in claim 1, wherein step a) includes determining a different RF amplitude modulation and RF phase modulation for each channel in the multichannel RF coil.

3. The method as recited in claim 1, wherein step b) includes transmitting multiband RF pulse waveforms using a single channel transmitter before splitting the multiband RF pulse waveforms into the multiple different channels of the multichannel RF coil, at which time each multiband RF pulse waveform is subjected to a channel-specific amplitude and phase change determined by the RF amplitude modulations and RF phase modulations determined in step a).

4. The method as recited in claim 1, wherein step b) includes independently controlling each channel in the multichannel RF coil to generate a multiband RF pulse using the RF amplitude modulations and the RF phase modulation determined for that channel in step a).

5. The method as recited in claim 1, wherein step a) includes:
   a)i) selecting a multiband factor that defines a number of slices to be excited by each multiband RF pulse;
   a)ii) determining a number of multiband RF pulses to be designed;
   a)iii) defining a plurality of slabs to be excited based on the selected multiband factor and the determined number of multiband RF pulses; and
   wherein step b) includes generating a plurality of multiband RF pulses, directing the MRI system to generate a plurality of multiband RF pulses using the RF amplitude modulations and RF phase modulations determined in step a), whereby the plurality of multiband RF pulses excite the plurality of slabs defined in step a)iii).

6. The method as recited in claim 1, wherein step a) includes determining each RF amplitude modulation and each RF phase modulation using a single spoke trajectory in k-space.

7. The method as recited in claim 1, wherein step a) includes determining an RF amplitude modulation and an RF phase modulation for each of a plurality of different spoke trajectories in k-space.

8. A method for directing a magnetic resonance imaging (MRI) system to generate a plurality of multiband radiofrequency (RF) pulses, the steps of the method comprising:
   a) selecting a multiband factor that defines a number of slices to be excited by each multiband RF pulse;
   b) determining a number of multiband RF pulses to be designed;
   c) defining a plurality of slabs to be excited based on the selected multiband factor and the determined number of multiband RF pulses;
   d) determining a number of RF amplitude modulations and a number of RF phase modulations for each channel in a multichannel RF coil by minimizing an objective function that includes:
      a complex-valued vector that contains the RF amplitude modulation and the RF phase modulation for each multiband RF pulse; and
      a system matrix that accounts for a spatial sensitivity profile of each channel in the multichannel RF coil, a magnetic field map for each excitation band in each multiband RF pulse, and a number of magnetic field gradients for each multiband RF pulse; and
   e) directing the MRI system to generate a plurality of multiband RF pulses using the RF amplitude modulations and RF phase modulations determined in step d), whereby the plurality of multiband RF pulses excite the plurality of slabs defined in step c).

9. The method as recited in claim 8, wherein step c) includes defining a spatial location for each slab and an order in which each slab is to be excited.

10. The method as recited in claim 9, wherein step c) includes defining the order as an interleaved order.

11. The method as recited in claim 9, wherein step c) further includes defining a spatial location for each of a plurality of slices located within each slab.

12. The method as recited in claim 10, wherein the spatial locations for the plurality of slices are equally distributed in each slab.

13. A method for simultaneously exciting multiple different slice locations in a subject using a magnetic resonance imaging (MRI) system, the steps of the method comprising:
   a) computing a multiband radio frequency (RF) pulse waveform to be applied to each channel in a multichannel RF coil;
   b) simultaneously computing a transmit-channel specific RF magnitude modulation for each channel in the multichannel transmitter and computing a transmit-channel specific RF phase modulation for each channel in the multichannel transmitter by minimizing an objective function that includes:
      a complex-valued vector that contains the transmit-channel specific RF amplitude modulation and the transmit-channel specific RF phase modulation for each transmit channel; and
      a system matrix that accounts for a spatial sensitivity profile of each channel in the multichannel RF coil, a magnetic field map for each excitation band in each multiband RF pulse, and a magnetic field gradient for each multiband RF pulse;
   c) directing the MRI system to generate an RF excitation field by, for each transmit channel, applying the transmit-channel magnitude and the transmit-channel phase for a given transmit channel to the computed multiband RF pulse waveform for the given transmit channel, thereby exciting spins in the multiple different slice locations in the subject.

14. The method as recited in claim 13, wherein each transmit-channel specific RF magnitude modulation is a same global RF magnitude modulation, and each transmit-channel specific RF phase modulation is a same global RF phase modulation.

15. The method as recited in claim 13, wherein the magnetic field gradient for each multiband RF pulse defines a same k-space trajectory.

16. The method as recited in claim 15, wherein the same k-space trajectory is a spoke trajectory.

17. The method as recited in claim 13, wherein the magnetic field gradient for each multiband RF pulse defines a different k-space trajectory.

* * * * *

UNITED STATES PATENT AND TRADEMARK OFFICE
CERTIFICATE OF CORRECTION

PATENT NO. : 10,684,337 B2  
APPLICATION NO. : 14/762093  
DATED : June 16, 2020  
INVENTOR(S) : Xiaoping Wu et al.

Page 1 of 2

It is certified that error appears in the above-identified patent and that said Letters Patent is hereby corrected as shown below:

In the Specification

Column 10, Line 34, "TSAR" should be -- *lSAR* --.

Column 11, Eq. (18), " $\left(\frac{\Delta t}{T}\sum_{i=1}^{N}|b(t_i)|^2\right)\cdot\left(\sum_{k=1}^{K}N_k\cdot\sum_{m=1}^{M}\sum_{s=1}^{S}w_{(k,m,s)}^{H}Qw_{(k,m,s)}\right)\leq gSAR;$ " should be -- $\left(\frac{\Delta t}{T}\sum_{i=1}^{N}|b(t_i)|^2\right)\cdot\left(\sum_{k=1}^{K}N_k\cdot\sum_{m=1}^{M}\sum_{s=1}^{S}w_{(k,m,s)}^{H}Qw_{(k,m,s)}\right)\leq gSAR;$ --.

Column 11, Eq. (19), " $\left(\frac{\Delta t}{T}\sum_{i=1}^{N}|b(t_i)|^2\right)\cdot\left(\sum_{k=1}^{K}N_k\cdot\sum_{m=1}^{M}\sum_{s=1}^{S}w_{(k,m,s)}^{H}S_v w_{(k,m,s)}\right)\leq lSAR, v=1,2,\ldots,V$ " should be -- $\left(\frac{\Delta t}{T}\sum_{i=1}^{N}|b(t_i)|^2\right)\cdot\left(\sum_{k=1}^{K}N_k\cdot\sum_{m=1}^{M}\sum_{s=1}^{S}w_{(k,m,s)}^{H}S_v w_{(k,m,s)}\right)\leq lSAR, v=1,2,\ldots,V$ --.

Column 11, Eq. (20), " $\left(\frac{\Delta t}{T}\sum_{i=1}^{N}|b(t_i)|^2\right)\cdot\left(\sum_{k=1}^{K}N_k\cdot\sum_{m=1}^{M}\sum_{s=1}^{S}|w_{(k,m,c,s)}|^2\right)\leq P_{ave}, c=1,2,\ldots,C;$ " should be -- $\left(\frac{\Delta t}{T}\sum_{i=1}^{N}|b(t_i)|^2\right)\cdot\left(\sum_{k=1}^{K}N_k\cdot\sum_{m=1}^{M}\sum_{s=1}^{S}|w_{(k,m,c,s)}|^2\right)\leq P_{ave}, c=1,2,\ldots,C$ --.

Column 14, Eq. (32), " $\left(\frac{\Delta t}{T}\sum_{i=1}^{N}|b(t_i)|^2\right)\cdot\left(M\sum_{k=1}^{K}N_k\cdot\sum_{s=1}^{S}w_{(k,s)}^{H}Qw_{(k,s)}\right)\leq gSAR;$ " should be -- $\left(\frac{\Delta t}{T}\sum_{i=1}^{N}|b(t_i)|^2\right)\cdot\left(M\sum_{k=1}^{K}N_k\cdot\sum_{s=1}^{S}w_{(k,s)}^{H}Qw_{(k,s)}\right)\leq gSAR;$ --.

Signed and Sealed this  
First Day of September, 2020

Andrei Iancu  
*Director of the United States Patent and Trademark Office*

CERTIFICATE OF CORRECTION (continued)
U.S. Pat. No. 10,684,337 B2

Column 14, Eq. (33), "$\left(\frac{\Delta t}{T}\sum_{i=1}^{N}|b(t_i)|^2\right)\cdot\left(M\sum_{k=1}^{K}N_k\cdot\sum_{s=1}^{S}w_{(k,s)}^{H}S_v w_{(k,s)}\right) \leq lSAR, v=1,2,\ldots,V$" should be --$\left(\frac{\Delta t}{T}\sum_{i=1}^{N}|b(t_i)|^2\right)\cdot\left(M\sum_{k=1}^{K}N_k\cdot\sum_{s=1}^{S}w_{(k,s)}^{H}S_v w_{(k,s)}\right) \leq lSAR, v=1,2,\ldots,V$--.

Column 14, Eq. (34), "$\left(\frac{\Delta t}{T}\sum_{i=1}^{N}|b(t_i)|^2\right)\cdot\left(M\sum_{k=1}^{K}N_k\cdot\sum_{s=1}^{S}|w_{(k,c,s)}|^2\right) \leq P_{ave}, c=1,2,\ldots,C;$" should be --$\left(\frac{\Delta t}{T}\sum_{i=1}^{N}|b(t_i)|^2\right)\cdot\left(M\sum_{k=1}^{K}N_k\cdot\sum_{s=1}^{S}|w_{(k,c,s)}|^2\right) \leq P_{ave}, c=1,2,\ldots,C$--.

Column 15, Line 43, "$\left|\sum_{m=1}^{M}a_m(t_i)\right|$" should be --$\left|\sum_{m=1}^{M}a_m(t_i)\right|$--.